United States Patent
Stahmann et al.

(10) Patent No.: US 9,433,368 B2
(45) Date of Patent: Sep. 6, 2016

(54) LEADLESS PACEMAKER WITH TRIPOLAR ELECTRODE

(71) Applicant: Cardiac Pacemakers, Inc., St. Paul, MN (US)

(72) Inventors: Jeffrey E. Stahmann, Ramsey, MN (US); William J. Linder, Golden Valley, MN (US); Keith R. Maile, New Brighton, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 58 days.

(21) Appl. No.: 14/444,069

(22) Filed: Jul. 28, 2014

(65) Prior Publication Data

US 2015/0057558 A1 Feb. 26, 2015

Related U.S. Application Data

(60) Provisional application No. 61/869,156, filed on Aug. 23, 2013.

(51) Int. Cl.
| | |
|---|---|
| *A61N 1/375* | (2006.01) |
| *A61N 1/362* | (2006.01) |
| *A61B 5/042* | (2006.01) |
| *A61N 1/372* | (2006.01) |

(52) U.S. Cl.
CPC .............. *A61B 5/042* (2013.01); *A61N 1/375* (2013.01); *A61N 1/37205* (2013.01); *A61B 2562/0209* (2013.01); *A61N 1/3756* (2013.01)

(58) Field of Classification Search
CPC .............. A61N 1/368; A61N 1/3684; A61N 1/37205; A61N 1/37288; A61N 1/3756
USPC ........................ 607/9, 32, 126, 127
See application file for complete search history.

(56) References Cited

U.S. PATENT DOCUMENTS

| | | | | |
|---|---|---|---|---|
| 7,565,195 | B1 * | 7/2009 | Kroll ................. | A61N 1/37288 607/2 |
| 8,019,419 | B1 * | 9/2011 | Panescu ................. | A61N 1/05 607/33 |
| 8,352,025 | B2 | 1/2013 | Jacobson | |
| 2004/0147973 | A1 * | 7/2004 | Hauser .................. | A61N 1/056 607/36 |
| 2006/0085041 | A1 * | 4/2006 | Hastings .............. | A61N 1/0587 607/33 |
| 2007/0293904 | A1 * | 12/2007 | Gelbart ................ | A61N 1/3785 607/35 |
| 2009/0082828 | A1 * | 3/2009 | Ostroff ............... | A61N 1/37205 607/36 |
| 2011/0282423 | A1 * | 11/2011 | Jacobson ............ | A61N 1/3704 607/126 |
| 2012/0078322 | A1 * | 3/2012 | Dal Molin .......... | A61B 5/0028 607/32 |
| 2012/0158111 | A1 * | 6/2012 | Khairkhahan ........ | A61N 1/375 607/127 |
| 2013/0116738 | A1 * | 5/2013 | Samade ............... | A61N 1/3756 607/3 |
| 2013/0324825 | A1 * | 12/2013 | Ostroff .................. | A61B 5/042 600/374 |

* cited by examiner

*Primary Examiner* — Allen Porter, Jr.
(74) *Attorney, Agent, or Firm* — Seager, Tufte & Wickhem LLP

(57) ABSTRACT

A leadless implantable medical device comprises a first electrode configured to deliver electrical pacing energy, a second electrode configured to sense intrinsic electrical cardiac activity, and a third electrode configurable to both deliver electrical pacing energy and sense intrinsic electrical cardiac activity. The first and third electrodes are used for delivering electrical pacing energy and the second and third electrodes are used to sense intrinsic electrical cardiac activity. None of the first, second and third electrodes are incorporated into a lead.

19 Claims, 3 Drawing Sheets

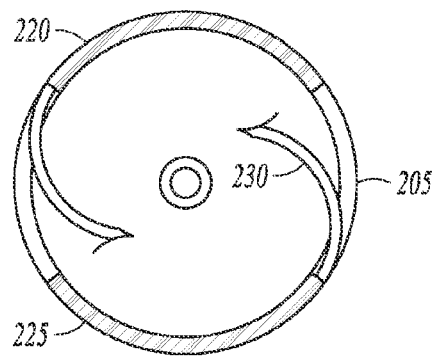
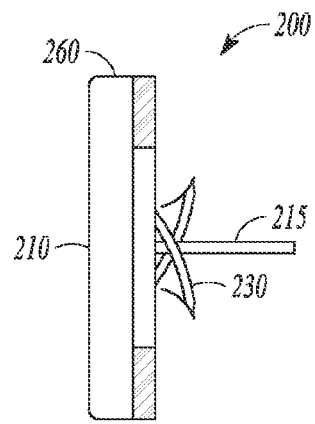
*FIG. 2A*                *FIG. 2B*
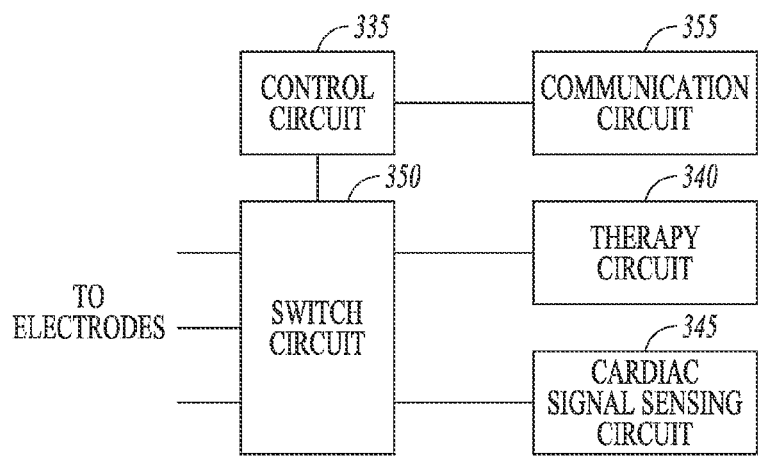
*FIG. 3*
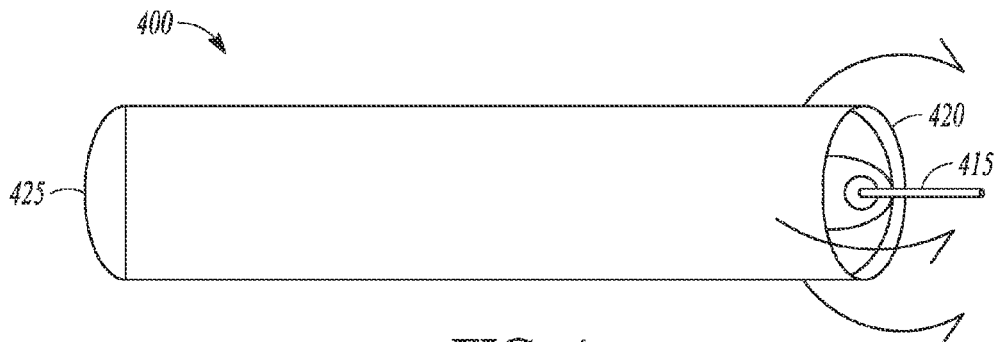
*FIG. 4*

US 9,433,368 B2

LEADLESS PACEMAKER WITH TRIPOLAR ELECTRODE

CLAIM OF PRIORITY

This application claims the benefit of priority under 35 U.S.C. §119(e) of U.S. Provisional Patent Application Ser. No. 61/869,156, filed on Aug. 23, 2013, which is herein incorporated by reference in its entirety.

BACKGROUND

Implantable medical devices can include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters.

Implantable medical devices typically include one or more implantable leads that can be positioned to contact the endocardium within one or more heart chambers or positioned to contact the epicardium. The leads include one or more electrodes to deliver electrical stimulation therapy or to sense intrinsic cardiac activity. The leads can be a source of potential device malfunction due to mechanical or electrical failure. An implantable device also typically includes electronics unit within a hermetically sealed housing. The electromechanical interface between the leads and the electronics unit can also be a source of potential device malfunction.

A leadless approach for endocardial pacing can address some of the challenges associated with implantable leads. However, this approach includes conflicting requirements to minimize electrode area for stimulation yet maximize electrode area for sensing. The present inventors have recognized a need for improved electrode design in leadless pacemakers.

OVERVIEW

This document relates generally to systems, devices, and methods that provide leadless electrical pacing therapy to the heart of a patient or subject. An example of a leadless implantable medical device includes a first electrode configured to deliver electrical pacing energy, a second electrode configured to sense intrinsic electrical cardiac activity, and a third electrode configurable to both deliver electrical pacing energy and sense intrinsic electrical cardiac activity. The first and third electrodes can be used for delivering electrical pacing energy and the second and third electrodes can be used to sense intrinsic electrical cardiac activity. None of the first, second and third electrodes are incorporated into a lead.

This section is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

FIGS. 2A and 2B illustrate portions of another example of a leadless implantable medical device.

FIG. 3 is a block diagram of portions of an example of a leadless implantable medical device.

FIG. 4 illustrates portions of another example of a leadless implantable medical device.

DETAILED DESCRIPTION

An implantable medical device may include one or more of the features, structures, methods, or combinations thereof described herein. For example, an implantable cardiac monitor or cardiac stimulator may be implemented to include one or more of the advantageous features or processes described below. It is intended that such a monitor, stimulator, or other implantable, partially implantable, or wearable device need not include all of the features described herein, but may be implemented to include selected features that provide for unique structures or functionality. Such a device may be implemented to provide a variety of therapeutic or diagnostic functions.

Figure 1:
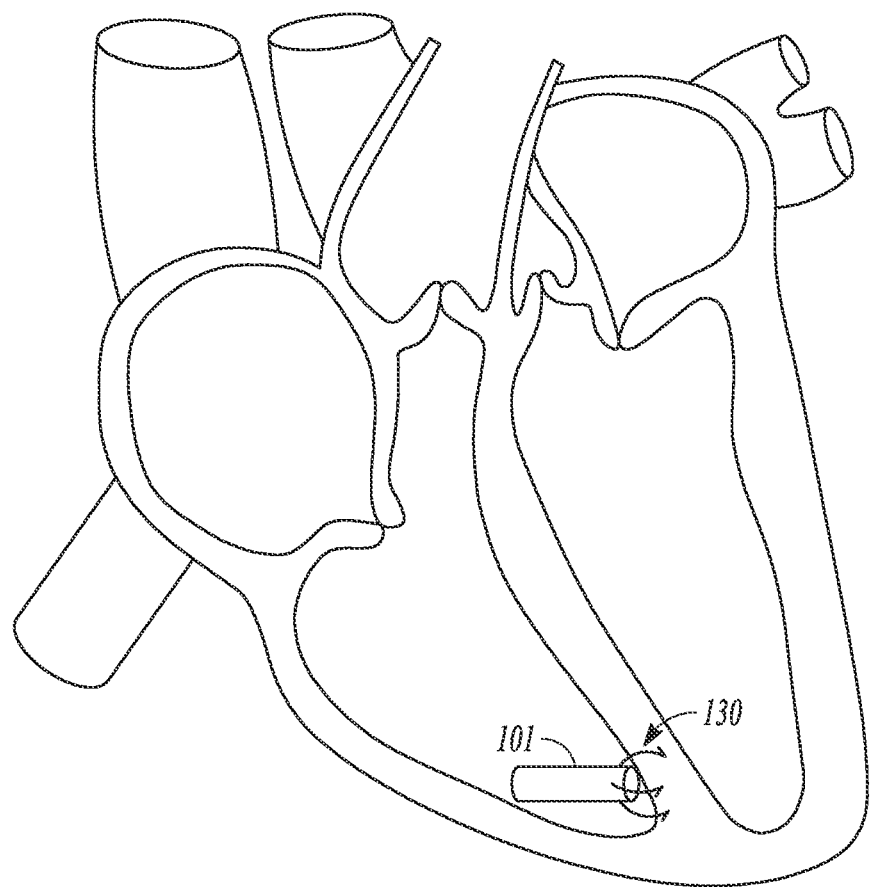
FIG. 1 illustrates an example of a leadless pacemaker.

This document discusses systems, devices and methods for improved leadless cardiac stimulators and leadless cardiac diagnostic devices. FIG. 1 shows an example of a leadless pacemaker 101. The leadless device is shown positioned at the endocardium within a ventricular chamber. The leadless device has a rod or bullet shape and includes electrodes arranged along the cylindrical portion of the housing. The leadless pacemaker 101 may include a mechanism 130 to fix the pacemaker into the myocardium. Examples of the fixation mechanism include one or more tines that extend radially from the housing, barbed tines, and a helix-shaped tine.

FIGS. 2A and 2B illustrate portions of an example of a leadless implantable medical device 200. The device is used to provide electrical pacing therapy and to sense intrinsic cardiac activity. FIG. 2A illustrates a front view 205 and FIG. 2B illustrates a side view 210. The leadless implantable medical device 200 includes a first electrode 215 used to deliver electrical pacing therapy and a second electrode 220 used to sense intrinsic electrical cardiac activity. The leadless implantable medical device 200 also includes a third electrode 225 configurable to both deliver electrical pacing energy and sense intrinsic electrical cardiac activity. Note that none of the first, second and third electrodes are incorporated into a lead.

The design requirements for electrodes used for pacing and electrodes used for sensing can be conflicting. For instance, it may be desirable to design the area of a pacing cathode that contacts tissue or fluid to be small while it may be desirable for sensing electrodes to have a larger surface area for better sensitivity. The first electrode 215 may have a small area and can be configured as a cathode to deliver pacing therapy with the third electrode 225 configured as the anode for the electrode pair. Additionally, the surface area of the first and third electrodes can be configured such that the ratio of the area of the third electrode 225 to the area of first electrode 215 is large (e.g., greater than a ratio of 10 to 1, greater than a ratio of 20 to 1, etc.). In some examples, the first electrode 215 is incorporated into a pin and the delivery of energy from the cathode can be substantially at the end of the pin. The length of the pin may vary. The second electrode 220 can be used together with the third electrode 225 to sense intrinsic electrical cardiac activity. The leadless implantable medical device 200 may include an electronics unit to configure the third electrode between delivering pacing therapy and sensing intrinsic electrical signals.

From the preceding description, it can be seen that the leadless implantable medical device 200 can be a leadless pacemaker configured with separate pacing and sensing electrodes. The electrodes can be sized to optimize the pacing and sensing. The combined surface area of the second and third electrodes can be greater than the combined surface area of the first and third electrodes. Thus, the surface area of the available electrodes can be larger for sensing and the surface area of the available electrodes can be smaller for pacing.

Separation requirements for electrodes used in sensing and electrodes used in pacing can also be conflicting. For instance, it may be desirable to include more separation between sensing electrodes for better sensitivity while it may be desirable to have less separation between pacing electrodes. It can be seen in FIG. 2 that the separation between the first electrode 215 and the second electrode 220 is less than the separation between the second electrode 220 and the third electrode 225. In an illustrative example, the diameter of the housing of the device can be about 20 millimeters (20 mm) and the separation between the second electrode 220 and the third electrode 225 can be about 10 mm.

The leadless implantable medical device 200 includes a hermetically sealed housing, and an electronics unit arranged within the housing. The leadless implantable medical device 200 can also include a power source such as a primary cell battery, rechargeable battery, capacitor, or other power source. The electronics unit can include a control circuit. The control circuit can include a processor (e.g., a microprocessor) or the control circuit can include logic circuits to sequentially step through performable functions (e.g., a state machine).

FIG. 3 is a block diagram of portions of an example of a leadless implantable medical device that shows a control circuit 335, a therapy circuit 340 that provides electrical pacing therapy, and a cardiac signal sensing circuit 345. The therapy circuit 340 may provide electrical pacing therapy to treat bradycardia. In certain examples, the therapy circuit 340 provides anti-tachyarrhythmia pacing (ATP) therapy. The anti-tachyarrhythmia therapy by the leadless implantable medical device may be provided with one or both of anti-tachyarrhythmia cardioversion therapy and defibrillation therapy provided by a second separate device (e.g., a subcutaneously implantable cardioverter/defibrillator). The leadless implantable medical device may communicate with the second device using a communication circuit 355 to coordinate delivery of the anti-tachyarrhythmia therapies. The communication between devices may be wireless. In certain examples the leadless implantable medical device does not communicate with the second device.

Other combinations of electrodes can be used for delivering electrical pacing therapy. The therapy circuit 340 and the cardiac signal sensing circuit 345 can be in electrical communication with the electrodes through a switch circuit 350. The second electrode 220 of FIG. 2 is configurable by the control circuit 335 circuit and the switch circuit 350 to both deliver electrical pacing energy by electrical connection to the therapy circuit 340 and sense intrinsic electrical cardiac activity by electrical connection to the cardiac signal sensing circuit 345. The control circuit 335 can select the first electrode 215 of FIG. 2 and either one of the second electrode 220 or third electrode 225 as an electrode pair to deliver electrical pacing energy. In some examples, the control circuit 335 selects the first electrode 215 of FIG. 2 and both the second electrode 220 and the third electrode 225 as an electrode triad to deliver electrical pacing energy, and can select the second electrode 220 and the third electrode 225 as an electrode pair to sense intrinsic electrical cardiac activity.

The leadless implantable medical device 200 can include additional electrodes with the second and third electrode (e.g., a fourth electrode also included at the periphery of the device housing, or the second and third electrodes shown can each be divided to form fourth and fifth electrodes). Multiple electrodes can be configurable for both pacing and sensing. For example, the second electrode 220 and a fourth electrode may be configurable to both deliver electrical pacing energy and to sense intrinsic electrical cardiac activity. The control circuit 335 can select the first electrode and one of the second, third or fourth electrodes as an electrode pair to deliver electrical pacing energy, and can select at least two of the second, third and fourth electrodes for sensing intrinsic electrical cardiac activity. In certain examples, the control circuit 335 may select the first electrode and any combination of the second, third or fourth electrodes for delivery of electrical pacing energy.

According to some examples, the hermetically sealed housing of the leadless implantable medical device 200 is shaped and sized for implanting epicardially. in the example of FIG. 2, the housing is substantially disk-shaped or in the button shaped. The device 200 includes a fixation device 230 to anchor the housing on the epicardium. Examples of the fixation device 230 include one or more tines that extend radially from the housing, one or more barbed tines, and a helix-shaped tine. The first electrode 215 can be incorporated into a pin arranged substantially orthogonal to a surface of the hermetically sealed housing. The pin and the first electrode 215 can be configured by shape, size and material for insertion into the epicardium. In certain examples, the first electrode 215 is substantially incorporated into the whole pin giving the first electrode 215 a pin shape. in certain examples, the first electrode 215 is located substantially at the tip of the pin. In certain examples, the first electrode is incorporated into a pin that is flexible.

The second electrode 220 and the third electrode 225 can be incorporated into a surface of the hermetically sealed housing. The hermetically sealed housing can include a first surface and a second surface opposite the first surface and the pin arranged substantially orthogonal to the first surface. The second electrode 220 and the third electrode 225 can be incorporated into a periphery of the first surface as shown in FIG. 2. Placing the electrodes at the periphery increases the separation between the electrodes if they are used for sensing. The second electrode 220 and the third electrode 225 can be formed into a larger area of the first surface to increase electrode size, but this may decrease the separation between the electrodes. in some examples, the hermetically sealed housing includes a side surface 260, The second electrode 220 and the third electrode 225 can be arranged on the side surface 260.

According to some examples, the hermetically sealed housing of the leadless implantable medical device is shaped and sized for implanting endocardially. FIG. 4 illustrates portions of another example of a leadless implantable medical device 400. The hermetically sealed housing includes an elongate cylindrical body having a first surface as a first capped end of the elongate cylindrical body and a second surface as a second capped end of the elongate cylindrical body. The first electrode 415 is incorporated into a pin arranged substantially orthogonal to the first surface, the second electrode 420 is incorporated into the first surface, and the third electrode 425 is incorporated into the second surface. In certain examples, the second electrode 420 is a ring shaped electrode arranged substantially at a periphery of the first surface.

As in the example of FIG. 2, the first electrode 415 of FIG. 4 can be used to deliver electrical pacing energy and the second electrode 420 can be used to sense intrinsic electrical cardiac activity. The third electrode 425 can be configurable to both deliver electrical pacing energy and sense intrinsic electrical cardiac activity; such that the first and third electrodes can be used for delivering electrical pacing energy and the second and third electrodes can be used to sense intrinsic electrical cardiac activity. None of the first, second and third electrodes are incorporated into a lead. The leadless implantable medical device 400 may include a circuit as that shown in the example of FIG. 3 to configure the electrodes for one or both of pacing and sensing.

Figure 5:
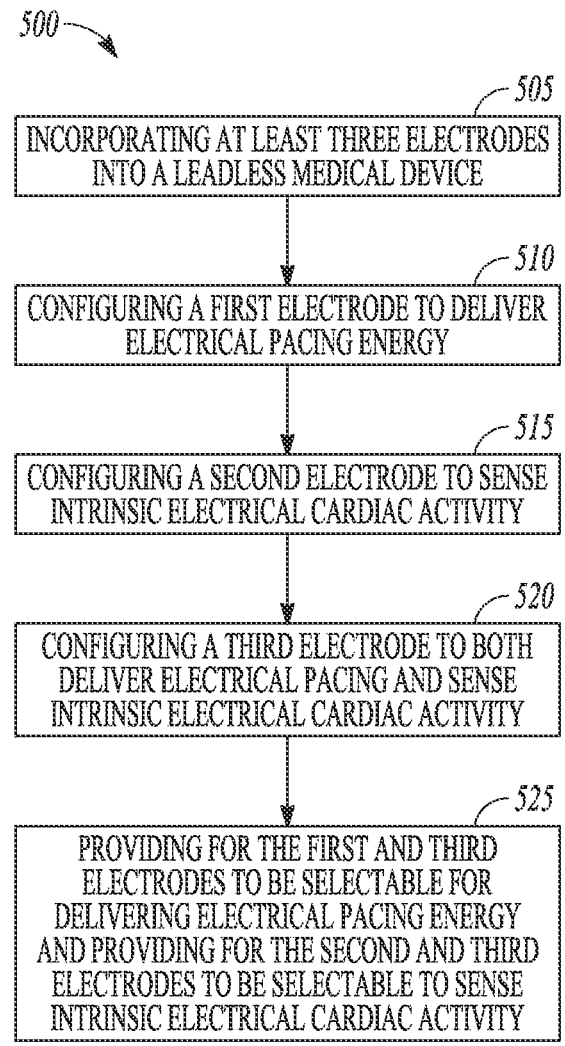
FIG. 5 is a flow diagram of an example of a method of making a leadless implantable medical device.

FIG. 5 is a flow diagram of an example of a method 500 of making a leadless implantable medical device. At block 505, at least three electrodes are incorporated into a leadless medical device. The electrodes can be incorporated into the housing of the device. In some examples, the housing is shaped and sized for epicardial placement, and in some examples the housing is shaped and sized for endocardial placement.

At block 510, the first electrode of the three electrodes can be configured by shape, size and position to deliver electrical pacing energy. In certain examples, a pin is arranged on a first surface of the housing to be substantially orthogonal to the first surface of the housing, and the first electrode is included in the pin. At block 515, the second of the three electrodes can be configured by shape, size and position to sense intrinsic electrical cardiac activity. The second electrode can be incorporated into the first surface.

At block 520, the third electrode of the three electrodes can be configured by shape, size and position to both deliver electrical pacing energy and sense intrinsic electrical cardiac activity. In certain examples, the third electrode is arranged on the first surface of the housing, and in certain examples, the third electrode is arranged on a second surface of the housing that is opposite the first surface. None of the first, second and third electrodes are incorporated into a lead.

At block 525, the first and third electrodes are made to be selectable for delivering electrical pacing energy, and the second and third electrodes are made to be selectable to sense intrinsic electrical cardiac activity. The select-ability can be provided by including a controllable (e.g., programmable) switch circuit network into an electronics unit arranged within the device housing.

The systems, devices, and methods described herein include examples of implantable medical devices without leads. The exclusion of leads removes the interface at the leads which can improve reliability. Different sets of electrodes are used for pacing therapy and for sensing. Position and size of the electrodes can be optimized independently to optimize the sensing of intrinsic signals and the delivery of pacing therapy. The examples have mostly been described in regard to leadless cardiac pacemakers. However, the examples can be equally useful in other types of leadless implantable devices that use electrodes for sensing and energy delivery, such as in neuro-stimulation devices intended to treat pain, heart failure, hypertension, or epilepsy that use electrodes to deliver energy or neuro-stimulation and monitor a physiological parameter.

ADDITIONAL NOTES

The above detailed description includes references to the accompanying drawings, which form a part of the detailed description. The drawings show, by way of illustration, specific embodiments in which the disclosure can be practiced. These embodiments are also referred to herein as "examples." In the event of inconsistent usages between this document and any documents incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure, This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the fill scope of equivalents to which such claims are entitled.

What is claimed is:

1. A leadless implantable medical device comprising:
a first electrode sized and configured to deliver electrical pacing energy as a pacing cathode electrode;
a second electrode sized and configured to sense intrinsic electrical cardiac activity; and
a third electrode sized and configured to sense intrinsic electrical cardiac activity in combination with the second electrode;
wherein the leadless implantable medical device is configured to use the second electrode and the third electrode as pacing anode electrodes in combination with the first electrode as pacing cathode electrodes for delivering electrical pacing energy.

2. The leadless implantable medical device of claim 1, wherein the combined surface area of the second and third electrodes is greater than the combined surface area of the first and third electrodes.

3. The leadless implantable medical device of claim 1, wherein a separation between the first electrode and the second electrode is less than a separation between the second electrode and the third electrode.

4. The leadless implantable medical device of claim 1, further comprising a control circuit, wherein the control circuit is configured to select the first electrode as the pacing cathode electrode and both the second and third electrodes as pacing anode electrodes to deliver electrical pacing energy, and to select the second and third electrodes as an electrode pair to sense intrinsic electrical cardiac activity.

5. The leadless implantable medical device of claim 1, comprising a hermetically sealed housing shaped and sized for implanting epicardially.

6. The leadless implantable medical device of claim 5, wherein the first electrode is incorporated into a pin arranged substantially orthogonal to a surface of the hermetically sealed housing, wherein the pin and the first electrode are configured for insertion into epicardial tissue.

7. The leadless implantable medical device of claim 6, wherein the pin is flexible.

8. The leadless implantable medical device of claim 5, wherein the second and third electrode are incorporated into a surface of the hermetically sealed housing and the first electrode is incorporated into a pin arranged substantially orthogonal to the surface of the hermetically sealed housing.

9. The leadless implantable medical device of claim 5, wherein the hermetically sealed housing has a disk-like shape and includes a first surface, a second surface opposite the first surface, and a side surface extending between the first surface and the second surface, and wherein the second and third electrodes are arranged on the side surface and the first electrode is incorporated into a pin arranged substantially orthogonal to the first surface.

10. The leadless implantable medical device of claim 1, comprising a hermetically sealed housing shaped and sized for implanting endocardially.

11. The leadless implantable medical device of claim 10, wherein the hermetically sealed housing includes an elongate cylindrical body having a first surface as a first capped end of the elongate cylindrical body and a second surface as a second capped end of the elongate cylindrical body, wherein the first electrode is incorporated into a pin arranged substantially orthogonal to the first surface, the second electrode is incorporated into the first surface, and the third electrode is incorporated into the second surface.

12. The leadless implantable medical device of claim 10, wherein the second electrode is a ring shaped electrode arranged substantially at a periphery of the first surface.

13. A method comprising:
incorporating at least three electrodes into a leadless medical device;
configuring a first electrode to deliver electrical pacing energy as a pacing cathode electrode;
configuring a second electrode to sense intrinsic electrical cardiac activity; and
configuring a third electrode to sense intrinsic electrical cardiac activity;
selecting the first electrode as a pacing cathode electrode and selecting the second and third electrodes as pacing anode electrodes; and
delivering electrical pacing energy using the first electrode as the pacing cathode electrode and the second and third electrodes as pacing anode electrodes.

14. The method of claim 13, comprising:
placing an electronics unit within a hermetically sealed housing that is substantially disk shaped; and
incorporating the second and third electrodes within one or more surfaces of the hermetically sealed housing and arranging the first electrode substantially orthogonal to a surface of the hermetically sealed housing.

15. The method of claim 14, comprising arranging the second and third electrode to have more separation than the second and first electrode.

16. The method of claim 13, comprising incorporating a control unit within the electronics unit and configuring the control unit to: select the first electrode as the pacing cathode electrode and both the second or third electrodes as pacing anode electrodes to deliver electrical pacing energy; and select the second and third electrodes to sense intrinsic electrical cardiac activity.

17. The method of claim 13, comprising:
placing an electronics unit within a hermetically sealed housing that is cylindrical and elongate, wherein the hermetically sealed housing includes a first surface as a first capped end of the elongate cylindrical body and a second surface as a second capped end of the elongate cylindrical body opposite the first capped end;
arranging the first electrode substantially orthogonal to the first surface;
incorporating the second electrode into the first surface; and
incorporating the third electrode into the second surface.

18. A leadless implantable medical device comprising:
a first electrode configured as a pacing cathode electrode having a first electrode surface area;
a second electrode configured as a pace/sense electrode having a second electrode surface area;
a third electrode configured as a pace/sense electrode having a third electrode surface area; and
a control circuit configured to select the first electrode as the pacing cathode electrode and both the second electrode and the third electrode as pacing anode electrodes for delivering electrical pacing energy;
the control circuit further configured to select the second electrode and the third electrode as an electrode pair for sensing intrinsic electrical cardiac activity;

wherein the third electrode surface area is at least ten times the first electrode surface area.

19. The leadless implantable medical device of claim 18, wherein the second electrode surface area is greater than the first electrode surface area.

* * * * *